US00PP08048P

United States Patent [19]

van der Knaap

[11] Patent Number: Plant 8,048

[45] Date of Patent: Nov. 24, 1992

[54] CHRYSANTHEMUM PLANT—YELLOW BOSSHARDT CULTIVAR

[75] Inventor: Jacques C. M. van der Knaap, DeLier, Netherlands

[73] Assignee: Fides Beheer B.V., De Lier, Netherlands

[21] Appl. No.: 680,138

[22] Filed: Apr. 3, 1991

[51] Int. Cl.[5] ..... A01H 5/00

[52] U.S. Cl. ..... Plt./78

[58] Field of Search ..... Plt./74, 74.1, 82.2

[56] References Cited

U.S. PATENT DOCUMENTS

P.P. 4,272 6/1978 Jessel, Jr. et al. ..... Plt. 78
P.P. 5,323 11/1984 Duffett ..... Plt. 74
P.P. 6,954 7/1989 VandenBerg ..... Plt. 74

*Primary Examiner*—Howard J. Locker

*Attorney, Agent, or Firm*—Burns, Doane, Swecker & Mathis

[57] ABSTRACT

A new and distinct cultivar of Chrysanthemum plant named Yellow Bosshardt is provided. The new cultivar was the result of a mutation induced by controlled irradiation with x-rays and can be readily distinguished from the parent Majoor Bosshardt cultivar (U.S. Plant patent application Ser. No. 07/680,136, filed concurrently herewith). More specifically, the new cultivar forms attractive large light yellow anemone-centered flowers having a green center when immature. The inflorescence tends to be pyramidal in configuration. The response period of the flowers is approximately eight weeks. The new cultivar is particularly suited for use in the production of a cut anemone spray under greenhouse conditions.

1 Drawing Sheet

SUMMARY OF THE INVENTION

The present invention comprises a new and distinct cultivar of Chrysanthemum, botanically known as *Dendranthema morifolium* Ramat., previously, *Chrysanthemum morifolium,* Ramat., and hereinafter is referred to by the cultivar name Yellow Bosshardt.

The new cultivar is a mutation which was induced in a plant of the Majoor Bosshardt cultivar (U.S. Plant patent application Ser. No. 07/680,136, filed concurrently herewith) by irradiation with x-rays at a level of 1750 rads. The parent Majoor Bosshardt cultivar typically forms flowers wherein the ray florets are white. The ability to produce the presently claimed mutation in a plant of the Majoor Bosshardt cultivar by any means was heretofore totally unknown and was incapable of prediction with certainty. The discovery of the new cultivar was made at De Lier, The Netherlands, during December, 1987.

It was observed that following the irradiation a single plant consistently formed flowers having a distinctive light yellow coloration. All other characteristics of the plant were found to be substantially identical to those of the Majoor Bosshardt cultivar. Had I not discovered, carefully studied, and preserved this new cultivar, it would have been lost to mankind. This new cultivar is particularly well suited for growing in the production of a cut anemone spray.

It was found that the new cultivar of the present invention:

(a) exhibits attractive relatively large anemone-centered flowers having an overall diameter of approximately 60 to 65 mm. wherein the ray florets are light yellow and the flower center comprising the disc florets is green in coloration when immature,
(b) bears flowers in a somewhat pyramidal configuration,
(c) exhibits a flower response period of approximately eight weeks, (d) forms dark green foliage, and
(e) has the ability to produce flowers of commercially acceptable quality throughout the year in a cut mum production program.

The keeping quality of the flowers is good, and partial resistance to leafminer is exhibited by the new cultivar.

Asexual reproduction of the new cultivar by cuttings as performed at De Lier, The Netherlands, in a controlled environment has demonstrated that the characteristics of the new cultivar as herein disclosed are firmly fixed and are retained through successive generations of asexual propagation.

Yellow Bosshardt has not been observed under all possible environmental conditions to date. Accordingly, it is possible that the phenotype may vary somewhat with variations in the environment, such as temperature, light, day length, contact with pesticides and/or subjection to growth retardant treatments.

When the new cultivar of the present invention is compared to the Majoor Bosshardt parent (U.S. Plant patent application Ser. No. 07/680,136, filed concurrently herewith), it is readily apparent that new cultivar possesses distinctive light yellow ray florets while the Majoor Bosshardt cultivar consistently forms white ray florets.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at De Lier, The Netherlands.

DETAILED DESCRIPTION

The chart used in the identification of colors described hereafter is The R.H.S. Colour Chart of the Royal Horiticultural Society, London, England. The color values were determined at 11:00 am. to 12:00 noon under natural daylight conditions at De Lier, The Netherlands, during October, 1988. The plants described were grown under standard greenhouse conditions which approximate those commonly utilized for the production of cut mums.

Classification:

*Botanical.*—*Dendranthema morifolium* Ramat., cv. Yellow Bosshardt.

*Commercial.*—Cut anemone spray.

Inflorescence

A. Capitulum:

*Form.*—Pyramidal.

*Type.*—Anemone.

*Diameter across face.*—Approximately 60 to 65 mm. on average.

*Diameter of disc.*—Approximately 17 mm. on average.

*Length of petals.*—Approximately 30 to 35 mm. on average.

B. Corolla of ray and disc florets:

*Color (General tonality from a distance of three meters).*—Yellow.

*Color ray florets.—(Top surface).*—Yellow Group 7D to Yellow Group 8D.

*Color disc florets.*—Yellow-Green Group 149A when immature changing to yellow when mature.

C. Reproductive organs:

*Androecium.*—Present in disc florets.

*Gynoecium.*—Present in both disc florets and ray florets.

Plant

A. General appearance:

*Height.*—Approximately 100 cm. on average.

B. Foliage:

*Color (upper surface).*—Yellow-Green Group 147A.

*Color (under surface).*—Yellow-Green Group 147B.

*Size.*—Approximately 80×70 mm.

I claim:

1. A new and distinct cultivar of Chrysanthemum plant named Yellow Bosshardt, substantially as herein shown and described, which:

(a) exhibits attractive relatively large anemone-centered flowers having an overall diameter of approximately 60 to 65 mm. wherein the ray florets are light yellow and the flower center comprising the disc florets is green in coloration when immature, (b) bears flowers in a somewhat pyramidal configuration, (c) exhibits a flower response period of approximately eight weeks, (d) forms dark green foliage, and (e) has the ability to produce flowers of commercially acceptable quality throughout the year in a cut mum production program.

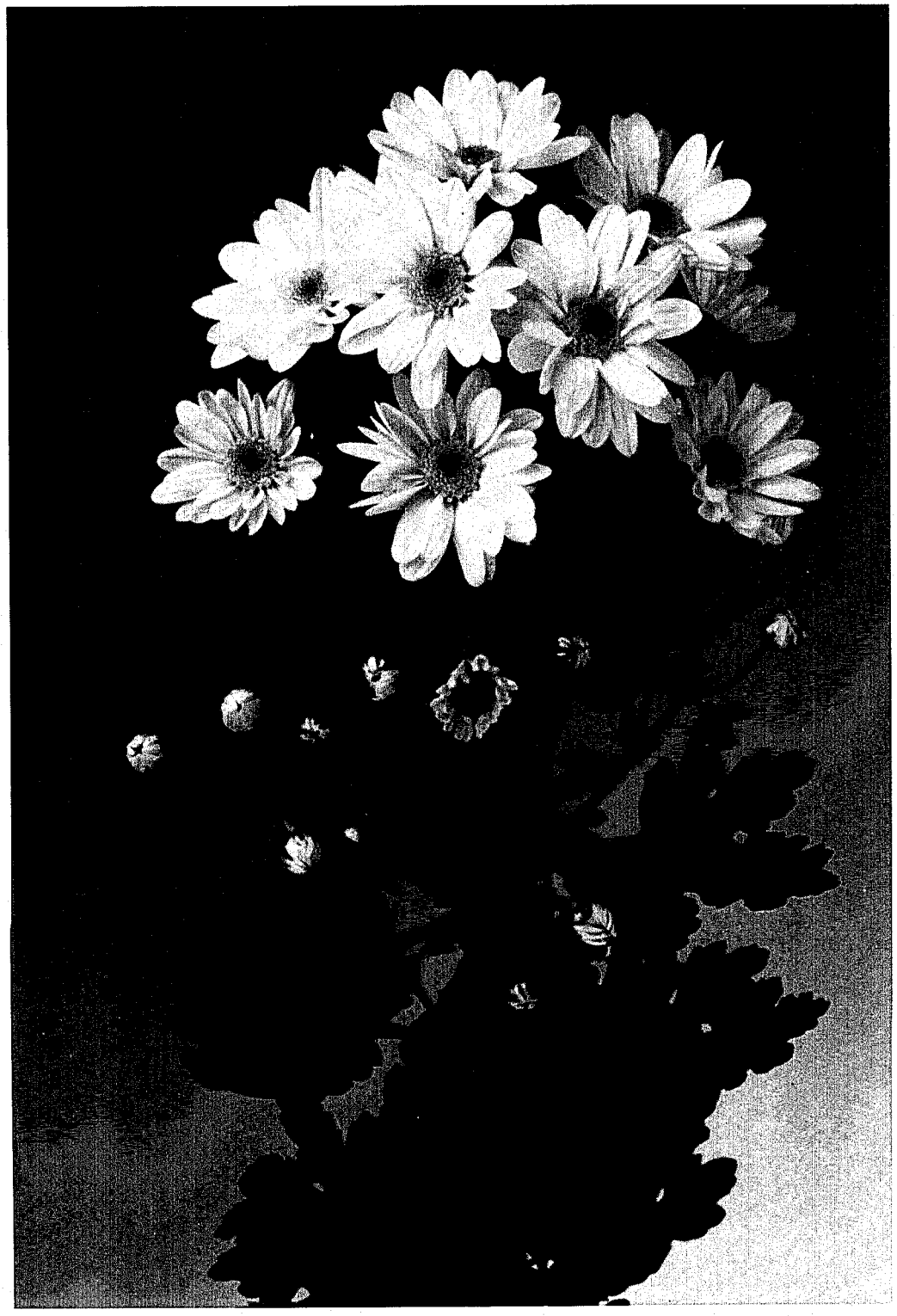

* * * * *